(12) United States Patent
Chen et al.

(10) Patent No.: US 12,226,233 B2
(45) Date of Patent: *Feb. 18, 2025

(54) PERSONALIZED BREAST IMAGING SYSTEM

(71) Applicant: Hologic, Inc., Marlborough, MA (US)

(72) Inventors: Biao Chen, Newark, DE (US); Haili Chui, Fremont, CA (US)

(73) Assignee: Hologic, Inc., Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/538,581

(22) Filed: Dec. 13, 2023

(65) Prior Publication Data
US 2024/0164720 A1    May 23, 2024

Related U.S. Application Data

(63) Continuation of application No. 16/942,268, filed on Jul. 29, 2020, now Pat. No. 11,883,206.
(Continued)

(51) Int. Cl.
*A61B 5/00* (2006.01)
*A61B 5/107* (2006.01)
(Continued)

(52) U.S. Cl.
CPC .............. *A61B 5/708* (2013.01); *A61B 5/004* (2013.01); *A61B 5/0073* (2013.01);
(Continued)

(58) Field of Classification Search
None
See application file for complete search history.

(56) References Cited

U.S. PATENT DOCUMENTS

| | | |
|---|---|---|
| 3,908,293 A | 9/1975 | Newman |
| 3,971,950 A | 7/1976 | Evans |
| (Continued) | | |

FOREIGN PATENT DOCUMENTS

| | | |
|---|---|---|
| CN | 1853573 | 11/2006 |
| CN | 101360453 | 2/2009 |
| (Continued) | | |

OTHER PUBLICATIONS

Blane, C. et al., "New Compression Paddle for Wire Localization in Mammography", Academic Radiology, 17(2): 142-145 (2010).
(Continued)

*Primary Examiner* — David P Porta
*Assistant Examiner* — Mamadou Faye
(74) *Attorney, Agent, or Firm* — Merchant & Gould P.C.

(57) ABSTRACT

Examples of the present disclosure describe systems and methods for personalized breast imaging. In aspects, a first set of patient attributes may be collected. The first set of patient attributes may relate to, or be used to determine, for example, breast size, breast thickness, and/or three-dimensional (3D) breast shape. The first set of patient attributes may be used to customize image acquisition parameters for the patient. A second set of patient attributes may also be collected. The second set of patient attributes may relate to, or be used to determine, for example, breast elasticity and breast density. The second set of patient attributes may be used to customize breast compression parameters for the patient. The customized image acquisition parameters and breast compression parameters may then be used to perform one or more procedures (e.g., an imaging procedure, a biopsy procedure, etc.) on the patient's breast.

20 Claims, 4 Drawing Sheets

Related U.S. Application Data

(60) Provisional application No. 62/879,758, filed on Jul. 29, 2019.

(51) Int. Cl.
*A61B 17/34* (2006.01)
*G06N 20/00* (2019.01)
*G06T 5/50* (2006.01)

(52) U.S. Cl.
CPC .......... *A61B 5/0077* (2013.01); *A61B 5/1072* (2013.01); *A61B 5/4312* (2013.01); *A61B 5/442* (2013.01); *A61B 17/3403* (2013.01); *G06N 20/00* (2019.01); *G06T 5/50* (2013.01); *G06T 2207/20221* (2013.01)

(56) References Cited

U.S. PATENT DOCUMENTS

| | | | |
|---|---|---|---|
| 4,821,727 A | 4/1989 | Levene et al. | |
| 4,907,156 A | 6/1990 | Doi et al. | |
| 5,078,142 A | 1/1992 | Siczek et al. | |
| 5,129,911 A | 7/1992 | Siczek et al. | |
| 5,133,020 A | 7/1992 | Giger et al. | |
| 5,219,351 A | 6/1993 | Teubner | |
| 5,220,867 A | 6/1993 | Carpenter | |
| 5,240,011 A | 8/1993 | Assa | |
| 5,280,427 A | 1/1994 | Magnusson | |
| 5,289,374 A | 2/1994 | Doi | |
| 5,289,520 A | 2/1994 | Pellegrino et al. | |
| 5,343,390 A | 8/1994 | Doi et al. | |
| 5,386,447 A | 1/1995 | Siczek | |
| 5,415,169 A | 5/1995 | Siczek et al. | |
| 5,426,685 A | 6/1995 | Pellegrino et al. | |
| 5,452,367 A | 9/1995 | Bick | |
| 5,474,072 A | 12/1995 | Schmulewitz | |
| 5,479,603 A | 12/1995 | Stone | |
| 5,491,627 A | 2/1996 | Zhang | |
| 5,495,576 A | 2/1996 | Ritchey | |
| 5,537,485 A | 7/1996 | Nishikawa | |
| 5,594,769 A | 1/1997 | Pellegrino et al. | |
| 5,609,152 A | 3/1997 | Pellegrino et al. | |
| 5,657,362 A | 8/1997 | Giger | |
| 5,729,471 A | 3/1998 | Jain | |
| 5,735,264 A | 4/1998 | Siczek et al. | |
| 5,769,086 A | 6/1998 | Ritchart et al. | |
| 5,773,832 A | 6/1998 | Sayed et al. | |
| 5,803,912 A | 9/1998 | Siczek et al. | |
| 5,851,180 A | 12/1998 | Crosby | |
| 5,872,828 A | 2/1999 | Niklason et al. | |
| 5,999,662 A | 12/1999 | Burt | |
| 6,022,325 A | 2/2000 | Siczek et al. | |
| 6,044,181 A | 3/2000 | Szeliski et al. | |
| 6,075,905 A | 6/2000 | Herman et al. | |
| 6,101,236 A | 8/2000 | Wang et al. | |
| 6,102,866 A | 8/2000 | Nields et al. | |
| 6,104,840 A | 8/2000 | Ejiri et al. | |
| 6,198,838 B1 | 3/2001 | Roehrig | |
| 6,245,028 B1 | 6/2001 | Furst et al. | |
| 6,249,616 B1 | 6/2001 | Hashimoto | |
| 6,263,092 B1 | 7/2001 | Roehrig | |
| 6,293,282 B1 | 9/2001 | Lemelson | |
| 6,349,153 B1 | 2/2002 | Teo | |
| 6,359,617 B1 | 3/2002 | Xiong | |
| 6,459,925 B1 | 10/2002 | Nields et al. | |
| 6,468,226 B1 | 10/2002 | McIntyre, IV | |
| 6,480,565 B1 | 11/2002 | Ning | |
| 6,620,111 B2 | 9/2003 | Stephens et al. | |
| 6,626,849 B2 | 9/2003 | Huitema et al. | |
| 6,638,235 B2 | 10/2003 | Miller et al. | |
| 6,683,934 B1 | 1/2004 | Zhao | |
| 6,725,095 B2 | 4/2004 | Fenn | |
| 6,758,824 B1 | 7/2004 | Miller et al. | |
| 6,987,331 B2 | 1/2006 | Koeppe | |
| 7,054,473 B1 | 5/2006 | Roehrig | |
| 7,123,684 B2 | 10/2006 | Jing et al. | |
| 7,134,080 B2 | 11/2006 | Kjeldsen | |
| 7,174,039 B2 | 2/2007 | Koo | |
| 7,184,582 B2 | 2/2007 | Giger et al. | |
| 7,245,694 B2 | 7/2007 | Jing et al. | |
| 7,466,795 B2 | 12/2008 | Eberhard et al. | |
| 7,489,761 B2 | 2/2009 | DeFreitas | |
| 7,505,555 B2 | 3/2009 | Hermann | |
| 7,577,282 B2 | 8/2009 | Gkanatsios et al. | |
| 7,606,801 B2 | 10/2009 | Faitelson et al. | |
| 7,616,801 B2 | 11/2009 | Gkanatsios et al. | |
| 7,634,050 B2 | 12/2009 | Muller et al. | |
| 7,697,660 B2 | 4/2010 | Ning | |
| 7,702,142 B2 | 4/2010 | Ren et al. | |
| 7,731,662 B2 | 6/2010 | Anderson et al. | |
| 7,760,924 B2 | 7/2010 | Ruth et al. | |
| 7,787,936 B2 | 8/2010 | Kressy | |
| 7,831,296 B2 | 11/2010 | DeFreitas et al. | |
| 7,869,563 B2 | 1/2011 | DeFreitas | |
| 7,889,896 B2 | 2/2011 | Roehrig | |
| 7,991,106 B2 | 8/2011 | Ren et al. | |
| 8,160,677 B2 | 4/2012 | Gielen et al. | |
| 8,192,361 B2 | 6/2012 | Sendai | |
| 8,465,413 B2 | 6/2013 | Deitch | |
| 8,532,745 B2 | 9/2013 | DeFreitas et al. | |
| 8,594,274 B2 | 11/2013 | Hoernig et al. | |
| 8,942,342 B2 | 1/2015 | Abenaim | |
| 9,019,262 B2 | 4/2015 | Ma | |
| 9,020,579 B2 | 4/2015 | Smith | |
| 9,160,793 B2 | 10/2015 | Base et al. | |
| 9,901,309 B2 | 2/2018 | DeFreitas et al. | |
| 9,901,320 B2 | 2/2018 | DeFreitas et al. | |
| 10,092,358 B2 | 10/2018 | DeFreitas | |
| 10,335,094 B2 | 7/2019 | DeFreitas | |
| 10,357,211 B2 | 7/2019 | Smith | |
| 10,456,213 B2 | 10/2019 | DeFreitas | |
| 10,595,954 B2 | 3/2020 | DeFreitas | |
| 10,733,566 B1 | 8/2020 | Chan | |
| 10,956,701 B2 | 3/2021 | Laviola | |
| 11,126,649 B2 | 9/2021 | Eswaran et al. | |
| 11,379,516 B2 | 7/2022 | Peng et al. | |
| 11,462,311 B2 | 10/2022 | Chan | |
| 11,853,401 B1 | 12/2023 | Nookula | |
| 11,883,206 B2 * | 1/2024 | Chen .................. | A61B 5/0073 |
| 2001/0038681 A1 | 11/2001 | Stanton et al. | |
| 2001/0044578 A1 | 11/2001 | Ben-Haim et al. | |
| 2002/0113681 A1 | 8/2002 | Byram | |
| 2002/0122533 A1 | 9/2002 | Marie et al. | |
| 2003/0007598 A1 | 1/2003 | Wang et al. | |
| 2003/0018272 A1 | 1/2003 | Treado et al. | |
| 2003/0055471 A1 | 3/2003 | Fenn et al. | |
| 2003/0073895 A1 | 4/2003 | Nields et al. | |
| 2003/0135115 A1 | 7/2003 | Burdette et al. | |
| 2003/0194050 A1 | 10/2003 | Eberhard et al. | |
| 2004/0077938 A1 | 4/2004 | Mark et al. | |
| 2004/0077944 A1 | 4/2004 | Steinberg | |
| 2004/0081273 A1 | 4/2004 | Ning | |
| 2004/0101095 A1 | 5/2004 | Jing | |
| 2004/0127789 A1 | 7/2004 | Ogawa | |
| 2004/0171933 A1 | 9/2004 | Stoller et al. | |
| 2004/0171986 A1 | 9/2004 | Tremaglio, Jr. et al. | |
| 2004/0267157 A1 | 12/2004 | Miller et al. | |
| 2005/0020903 A1 | 1/2005 | Krishnan et al. | |
| 2005/0049497 A1 | 3/2005 | Krishnan et al. | |
| 2005/0049521 A1 | 3/2005 | Miller et al. | |
| 2005/0084060 A1 | 4/2005 | Seppi et al. | |
| 2005/0089205 A1 | 4/2005 | Kapur | |
| 2005/0108643 A1 | 5/2005 | Schybergson | |
| 2005/0111718 A1 | 5/2005 | MacMahon | |
| 2005/0113681 A1 | 5/2005 | DeFreitas et al. | |
| 2005/0113715 A1 | 5/2005 | Schwindt et al. | |
| 2005/0124845 A1 | 6/2005 | Thomadsen et al. | |
| 2006/0009693 A1 | 1/2006 | Hanover et al. | |
| 2006/0025680 A1 | 2/2006 | Jeune-Iomme | |
| 2006/0030784 A1 | 2/2006 | Miller et al. | |
| 2006/0074287 A1 | 4/2006 | Neumann | |
| 2006/0098855 A1 | 5/2006 | Gkanatsios et al. | |
| 2006/0126794 A1 | 6/2006 | Hermann | |
| 2006/0129062 A1 | 6/2006 | Nicoson et al. | |

(56) References Cited

U.S. PATENT DOCUMENTS

| | | |
|---|---|---|
| 2006/0155209 A1 | 7/2006 | Miller et al. |
| 2006/0178601 A1 | 8/2006 | Wang |
| 2006/0257009 A1 | 11/2006 | Wang |
| 2006/0269040 A1 | 11/2006 | Mertelmeier |
| 2007/0019846 A1 | 1/2007 | Bullitt et al. |
| 2007/0114424 A1 | 5/2007 | Danielsson et al. |
| 2007/0167709 A1 | 7/2007 | Slayton |
| 2007/0225600 A1 | 9/2007 | Weibrecht et al. |
| 2007/0232882 A1 | 10/2007 | Glossop |
| 2007/0263765 A1 | 11/2007 | Wu |
| 2007/0280412 A1 | 12/2007 | DeFreitas |
| 2008/0019581 A1 | 1/2008 | Gkanatsios et al. |
| 2008/0045833 A1 | 2/2008 | DeFreitas et al. |
| 2008/0101537 A1 | 5/2008 | Sendai |
| 2008/0103834 A1 | 5/2008 | Reiner |
| 2008/0152086 A1 | 6/2008 | Hall |
| 2008/0181361 A1 | 7/2008 | Eldered |
| 2008/0187095 A1 | 8/2008 | Boone et al. |
| 2008/0198966 A1 | 8/2008 | Hjarn |
| 2008/0242968 A1 | 10/2008 | Claus et al. |
| 2009/0003519 A1 | 1/2009 | DeFreitas |
| 2009/0024030 A1 | 1/2009 | Lachaine |
| 2009/0080604 A1 | 3/2009 | Shores et al. |
| 2009/0118614 A1 | 5/2009 | Sendai |
| 2009/0124906 A1 | 5/2009 | Caluser |
| 2009/0143674 A1 | 6/2009 | Nields |
| 2009/0171244 A1 | 7/2009 | Ning |
| 2009/0175408 A1 | 7/2009 | Goodsitt et al. |
| 2009/0177495 A1 | 7/2009 | Abousy et al. |
| 2009/0296882 A1 | 12/2009 | Gkanatsios et al. |
| 2010/0016707 A1 | 1/2010 | Amara et al. |
| 2010/0034348 A1 | 2/2010 | Yu |
| 2010/0098214 A1 | 4/2010 | Star-Lack et al. |
| 2010/0135558 A1 | 6/2010 | Ruth et al. |
| 2010/0152570 A1 | 6/2010 | Navab |
| 2010/0166147 A1 | 7/2010 | Abenaim |
| 2010/0208037 A1 | 8/2010 | Sendai |
| 2011/0019891 A1 | 1/2011 | Puong |
| 2011/0069808 A1 | 3/2011 | Defreitas et al. |
| 2011/0087132 A1 | 4/2011 | DeFreitas et al. |
| 2011/0110576 A1 | 5/2011 | Kreeger |
| 2011/0182402 A1 | 7/2011 | Partain |
| 2011/0237927 A1 | 9/2011 | Brooks et al. |
| 2011/0257919 A1 | 10/2011 | Reiner |
| 2011/0268339 A1 | 11/2011 | Volokh |
| 2011/0313288 A1 | 12/2011 | Chi Sing |
| 2012/0014504 A1 | 1/2012 | Jang |
| 2012/0035462 A1 | 2/2012 | Maurer et al. |
| 2012/0050321 A1 | 3/2012 | Arieli |
| 2012/0134464 A1 | 5/2012 | Hoernig et al. |
| 2012/0150034 A1 | 6/2012 | DeFreitas et al. |
| 2012/0238870 A1 | 9/2012 | Smith et al. |
| 2012/0256920 A1 | 10/2012 | Marshall et al. |
| 2012/0259230 A1 | 10/2012 | Riley |
| 2012/0302887 A1 | 11/2012 | Anderson et al. |
| 2013/0022165 A1 | 1/2013 | Jang |
| 2013/0044861 A1 | 2/2013 | Muller |
| 2013/0090554 A1 | 4/2013 | Zvuloni |
| 2013/0108138 A1 | 5/2013 | Nakayama |
| 2013/0259193 A1 | 10/2013 | Packard |
| 2014/0064444 A1 | 3/2014 | Oh |
| 2014/0073913 A1 | 3/2014 | DeFreitas et al. |
| 2014/0328530 A1 | 11/2014 | Lee |
| 2015/0051489 A1 | 2/2015 | Caluser |
| 2015/0087984 A1 | 3/2015 | Tateyama |
| 2015/0182191 A1 | 7/2015 | Caluser et al. |
| 2015/0199478 A1 | 7/2015 | Bhatia et al. |
| 2015/0245817 A1 | 9/2015 | Stone |
| 2015/0324522 A1 | 11/2015 | Chan |
| 2015/0347693 A1 | 12/2015 | Lam et al. |
| 2015/0375399 A1 | 12/2015 | Chiu |
| 2016/0000399 A1 | 1/2016 | Halmann et al. |
| 2016/0022364 A1 | 1/2016 | DeFreitas et al. |
| 2016/0048958 A1 | 2/2016 | Miga et al. |
| 2016/0051215 A1 | 2/2016 | Chen |
| 2016/0074012 A1 | 3/2016 | Forzoni |
| 2016/0166217 A1 | 6/2016 | Davis |
| 2016/0216769 A1 | 7/2016 | Goetz |
| 2016/0235379 A1 | 8/2016 | Homann |
| 2016/0235380 A1 | 8/2016 | Smith |
| 2016/0317129 A1 | 11/2016 | Seip |
| 2016/0328998 A1 | 11/2016 | Pedersen |
| 2017/0181809 A1 | 6/2017 | Panescu |
| 2017/0185904 A1 | 6/2017 | Padmanabhan |
| 2017/0213131 A1 | 7/2017 | Hammond |
| 2017/0251991 A1 | 9/2017 | Wang |
| 2017/0265947 A1 | 9/2017 | Dyer |
| 2017/0340303 A1* | 11/2017 | Stango ............... A61B 90/17 |
| 2017/0364645 A1 | 12/2017 | Jester |
| 2018/0018590 A1 | 1/2018 | Szeto |
| 2018/0068066 A1 | 3/2018 | Bronkalla |
| 2018/0125446 A1 | 5/2018 | Boroczky |
| 2018/0249985 A1 | 9/2018 | DeFreitas |
| 2018/0256118 A1 | 9/2018 | DeFreitas |
| 2018/0286504 A1 | 10/2018 | Trovato |
| 2019/0015058 A1 | 1/2019 | Valenzuela |
| 2019/0015173 A1 | 1/2019 | DeFreitas |
| 2019/0064929 A1 | 2/2019 | Tomeh |
| 2019/0111282 A1 | 4/2019 | Yamada |
| 2019/0138693 A1 | 5/2019 | Muller et al. |
| 2019/0155633 A1 | 5/2019 | Faulhaber, Jr |
| 2019/0188848 A1 | 6/2019 | Madani et al. |
| 2019/0201106 A1 | 7/2019 | Siemionow et al. |
| 2019/0221304 A1 | 7/2019 | Ionasec |
| 2019/0295248 A1 | 9/2019 | Nakamura et al. |
| 2019/0328482 A1 | 10/2019 | Izmirili |
| 2020/0043600 A1 | 2/2020 | Glottmann et al. |
| 2020/0046303 A1 | 2/2020 | DeFreitas |
| 2020/0093562 A1 | 3/2020 | DeFreitas |
| 2020/0160510 A1 | 5/2020 | Lindemer |
| 2020/0167920 A1 | 5/2020 | Hall et al. |
| 2020/0205928 A1 | 7/2020 | DeFreitas |
| 2020/0211692 A1 | 7/2020 | Kalafut |
| 2020/0284591 A1 | 9/2020 | Shapira |
| 2020/0286613 A1 | 9/2020 | Rego |
| 2020/0311938 A1 | 10/2020 | Vincent |
| 2020/0345324 A1 | 11/2020 | Matsumoto |
| 2020/0352543 A1 | 11/2020 | DeFreitas |
| 2020/0357118 A1 | 11/2020 | Yao |
| 2020/0381125 A1 | 12/2020 | Hao et al. |
| 2020/0390404 A1 | 12/2020 | DeFreitas |
| 2021/0000553 A1 | 1/2021 | St. Pierre |
| 2021/0030366 A1 | 2/2021 | Chen |
| 2021/0035680 A1 | 2/2021 | Chen |
| 2021/0038921 A1 | 2/2021 | Nguyen |
| 2021/0098120 A1 | 4/2021 | Kshirsagar |
| 2021/0100626 A1 | 4/2021 | St. Pierre |
| 2021/0224508 A1 | 7/2021 | Laviola |
| 2021/0256289 A1 | 8/2021 | Kumagi |
| 2021/0303078 A1 | 9/2021 | Wells |
| 2021/0398650 A1 | 12/2021 | Baker |
| 2022/0000491 A1 | 1/2022 | Henry |
| 2022/0133258 A1 | 5/2022 | Yin et al. |
| 2022/0164586 A1 | 5/2022 | Chui |
| 2022/0164951 A1 | 5/2022 | Chui |
| 2022/0265387 A1 | 8/2022 | Daon |
| 2022/0405644 A1 | 12/2022 | Szeto |
| 2023/0098785 A1 | 3/2023 | St. Pierre |
| 2023/0351600 A1 | 11/2023 | Jing |
| 2024/0242820 A1 | 7/2024 | Kshirsagar |

FOREIGN PATENT DOCUMENTS

| | | |
|---|---|---|
| CN | 101517582 | 8/2009 |
| CN | 101959456 A | 1/2011 |
| CN | 202161328 | 3/2012 |
| CN | 102429678 | 5/2012 |
| CN | 102448375 | 5/2012 |
| CN | 102473300 A | 5/2012 |
| CN | 102855483 A | 1/2013 |
| CN | 105025799 A | 11/2015 |
| CN | 108140425 | 6/2018 |

(56) References Cited

FOREIGN PATENT DOCUMENTS

| | | |
|---|---|---|
| CN | 108492874 | 9/2018 |
| CN | 111584046 | 8/2020 |
| DE | 103 05 640 | 8/2003 |
| DE | 102011087127 | 5/2013 |
| EP | 1428473 | 6/2004 |
| EP | 2236085 | 6/2010 |
| EP | 2491863 | 8/2012 |
| EP | 1986548 | 1/2013 |
| EP | 2656789 | 10/2013 |
| EP | 3060132 | 4/2019 |
| JP | 2003-527880 | 9/2003 |
| JP | 2003-531516 | 10/2003 |
| JP | 2005125080 | 5/2005 |
| JP | 2006-505376 | 2/2006 |
| JP | 2006-519634 | 8/2006 |
| JP | 2007-130487 | 5/2007 |
| JP | 2007-515242 | 6/2007 |
| JP | 2008518722 | 6/2008 |
| JP | 2009502347 | 1/2009 |
| JP | 2009-522005 | 6/2009 |
| JP | 2009-157527 | 7/2009 |
| JP | 2009-526618 | 7/2009 |
| JP | 2010-137004 | 6/2010 |
| JP | 2011-508242 | 3/2011 |
| JP | 2012-501750 | 1/2012 |
| JP | 2014-507250 | 3/2014 |
| JP | 2015-506794 | 3/2015 |
| JP | 2015-065975 | 4/2015 |
| JP | 2016-035739 | 3/2016 |
| JP | 2019-170794 | 10/2019 |
| JP | 2020-048685 | 4/2020 |
| JP | 2020-156823 | 10/2020 |
| WO | 93/17620 | 9/1993 |
| WO | 94/06352 | 3/1994 |
| WO | 1997/00649 | 1/1997 |
| WO | 00/51484 | 9/2000 |
| WO | 0154463 | 7/2001 |
| WO | 2005/052838 | 6/2005 |
| WO | 2005/079306 | 9/2005 |
| WO | 2005/110230 | 11/2005 |
| WO | 2005/112767 | 12/2005 |
| WO | 2006/055830 | 5/2006 |
| WO | 2006/058160 | 6/2006 |
| WO | 2007/095330 | 8/2007 |
| WO | 08/014670 | 2/2008 |
| WO | 2008/054436 | 5/2008 |
| WO | 2009/026587 | 2/2009 |
| WO | 2010/028208 | 3/2010 |
| WO | 2011/043838 | 4/2011 |
| WO | 2011/063530 | 6/2011 |
| WO | 2012/001572 | 1/2012 |
| WO | 2012/068373 | 5/2012 |
| WO | 2012/073164 | 6/2012 |
| WO | 2012/112627 | 8/2012 |
| WO | 2012/122399 | 9/2012 |
| WO | 2013/001439 | 1/2013 |
| WO | 2013/078476 | 5/2013 |
| WO | 2013/123091 | 8/2013 |
| WO | 2014/194171 | 12/2014 |
| WO | 2015/061582 | 4/2015 |
| WO | 2016/103094 | 6/2016 |
| WO | 2016/184746 | 11/2016 |
| WO | 2017/058848 | 4/2017 |
| WO | 2017/218773 | 12/2017 |
| WO | 2019/030410 | 2/2019 |
| WO | 2019/060843 | 3/2019 |
| WO | 2016/057960 | 5/2019 |
| WO | 2019/091807 | 5/2019 |
| WO | 2019/102917 | 5/2019 |
| WO | 2019/227042 | 11/2019 |
| WO | 2018/221689 | 4/2020 |
| WO | 2020/216307 | 10/2020 |
| WO | 2021/168281 | 8/2021 |
| WO | 2021/195370 | 9/2021 |

OTHER PUBLICATIONS

Bram Van Ginneken, Computer-aided Diagnosis in Chest Radiography Thesis, Image Sciences Institute, University Medical Center Utrecht, Utrecht, Netherlands.

Carson, P. et al., "Local compression in automated breast ultrasound in the mammographic geometry", Ultrasonics Symposium, 1787-1790 (2010).

Gutierrez et al., "Multimodality image guidance system integrating X-ray fluoroscopy and ultrasound image streams with electromagnetic tracking", Medical Imaging 2007: Visualization and Image-Guided Procedures, Proc. of SPIE vol. 6509, 2007, pp. 1-10.

Vaartjes, S.E. et al., "First clinical trials of the twente photoacoustic mammoscope (PAM)", Visual Communications and Image Processing; Jan. 20, 2004, San Jose, CA, UDS, vol. 6629, Jan. 1, 2007, pp. 1-12.

"Filtered Back Projection", (NYGREN), published May 8, 2007, URL: http://web.archive.org/web/19991010131715/http://www.owlnet.rice.edu/~elec539/Projects97/cult/node2.html, 2 pgs.

"Supersonic to feature Aixplorer Ultimate at ECR", AuntiMinnie.com, 3 pages (Feb. 2018).

Berg, WA et al., "Combined screening with ultrasound and mammography vs mammography alone in women at elevated risk of breast cancer", JAMA 299:2151-2163, 2008.

Burbank, Fred, "Stereotactic Breast Biopsy: Its History, Its Present, and Its Future", published in 1996 at the Southeastern Surgical Congress, 24 pages.

Bushberg, Jerrold et al., "The Essential Physics of Medical Imaging", 3rd ed., In: "The Essential Physics of Medical Imaging, Third Edition", Dec. 28, 2011, Lippincott & Wilkins, Philadelphia, PA, USA, XP05579051, pp. 270-272.

Carton, AK, et al., "Dual-energy contrast-enhanced digital breast tomosynthesis—a feasibility study", Br J Radiol. Apr. 2010;83 (988):344-50.

Chen, SC, et al., "Initial clinical experience with contrast-enhanced digital breast tomosynthesis", Acad Radio. Feb. 2007 14(2):229-38.

Choi Bareum et al., "Surgical-tools detection based on Convolutional Neural Network in laparoscopic robot-assisted surgery", 2017 39th Annual International Conference of the IEEE Engineering in Medicine and Biology Society (EMBC), IEEE, Jul. 11, 2017, pp. 1756-1759.

Diekmann, F., et al., "Digital mammography using iodine-based contrast media: initial clinical experience with dynamic contrast medium enhancement", Invest Radiol 2005; 40:397-404.

Dromain C., et al., "Contrast enhanced spectral mammography: a multi-reader study", RSNA 2010, 96th Scientific Assembly and Scientific Meeting.

Dromain, C., et al., "Contrast-enhanced digital mammography", Eur J Radiol. 2009; 69:34-42.

Dromain, Clarisse et al., "Dual-energy contrast-enhanced digital mammography: initial clinical results", European Radiology, Sep. 14, 2010, vol. 21, pp. 565-574.

E. Shaw de Paredes et al., "Interventional Breast Procedure", published Sep./Oct. 1998 in Curr Probl Diagn Radiol, pp. 138-184.

Fischer Imaging Corp, Mammotest Plus manual on minimally invasive breast biopsy system, 2002, 8 pages.

Fischer Imaging Corporation, Installation Manual, MammoTest Family of Breast Biopsy Systems, 86683G, 86684G, P-55957-IM, Issue 1, Revision 3, Jul. 2005, 98 pages.

Fischer Imaging Corporation, Operator Manual, Mammo Test Family of Breast Biopsy Systems, 86683G, 86684G, P-55956-OM, Issue 1, Revision 6, Sep. 2005, 258 pages.

Freiherr, G., "Breast tomosynthesis trials show promise", Diagnostic Imaging—San Francisco 2005, V27; N4:42-48.

Georgian-Smith, Dianne, et al., "Stereotactic Biopsy of the Breast Using an Upright Unit, a Vacuum-Suction Needle, and a Lateral Arm-Support System", 2001, at the American Roentgen Ray Society meeting, 8 pages.

Giger et al. "Development of a smart workstation for use in mammography", in Proceedings of SPIE, vol. 1445 (1991), pp. 101103; 4 pages.

(56) References Cited

OTHER PUBLICATIONS

Giger et al., "An Intelligent Workstation for Computer-aided Diagnosis", in RadioGraphics, May 1993, 13:3 pp. 647-656; 10 pages.
Han et al., "MatchNet: Unifying Feature and Metric Learning for Patch-Based Matching", 2015 IEEE Conference on Computer Vision and Pattern Recognition (CVPR), Boston, MA, 2015, pp. 3279-3286.
Hologic, "Lorad StereoLoc II" Operator's Manual 9-500-0261, Rev. 005, 2004, 78 pgs.
Hologic, Inc., 510(k) Summary, prepared Nov. 28, 2010, for Affirm Breast Biopsy Guidance System Special 510(k) Premarket Notification, 5 pages.
Hologic, Inc., 510(k) Summary, prepared Aug. 14, 2012, for Affirm Breast Biopsy Guidance System Special 510(k) Premarket Notification, 5 pages.
ICRP Publication 60: 1990 Recommendations of the International Commission on Radiological Protection, 12 pages.
Jochelson, M., et al., "Bilateral Dual Energy contrast-enhanced digital mammography: Initial Experience", RSNA 2010, 96th Scientific Assembly and Scientific Meeting, 1 page.
Jong, RA, et al., Contrast-enhanced digital mammography: initial clinical experience. Radiology 2003; 228:842-850.
Koechli, Ossi R., "Available Sterotactic Systems for Breast Biopsy", Renzo Brun del Re (Ed.), Minimally Invasive Breast Biopsies, Recent Results in Cancer Research 173:105-113; Springer-Verlag, 2009.
Kopans, et al. Will tomosynthesis replace conventional mammography? Plenary Session SFN08: RSNA 2005.
Lehman, CD, et al. MRI evaluation of the contralateral breast in women with recently diagnosed breast cancer. N Engl J Med 2007; 356:1295-1303.
Lewin, JM, et al., Dual-energy contrast-enhanced digital subtraction mammography: feasibility. Radiology 2003; 229:261-268.
Lindfors, KK, et al., Dedicated breast CT: initial clinical experience. Radiology 2008; 246(3): 725-733.
Niklason, L., et al., Digital tomosynthesis in breast imaging. Radiology. Nov. 1997; 205(2):399-406.
Poplack, SP, et al., Digital breast tomosynthesis: initial experience in 98 women with abnormal digital screening mammography. AJR Am J Roentgenology Sep. 2007 189(3):616-23.
Prionas, ND, et al., Contrast-enhanced dedicated breast CT: initial clinical experience. Radiology. Sep. 2010 256(3):714-723.
Rafferty, E. et al., "Assessing Radiologist Performance Using Combined Full-Field Digital Mammography and Breast Tomosynthesis Versus Full-Field Digital Mammography Alone: Results" . . . presented at 2007 Radiological Society of North America meeting, Chicago IL.
Reynolds, April, "Stereotactic Breast Biopsy: A Review", Radiologic Technology, vol. 80, No. 5, Jun. 1, 2009, pp. 447M-464M, XP055790574.
Shrading, Simone et al., "Digital Breast Tomosynthesis-guided Vacuum-assisted Breast Biopsy: Initial Experiences and Comparison with Prone Stereotactic Vacuum-assisted Biopsy", the Department of Diagnostic and Interventional Radiology, Univ. of Aachen, Germany, published Nov. 12, 2014, 10 pgs.
Smith, A., "Full field breast tomosynthesis", Radiol Manage. Sep.-Oct. 2005; 27(5):25-31.
Weidner N, et al., "Tumor angiogenesis and metastasis: correlation in invasive breast carcinoma", New England Journal of Medicine 1991; 324:1-8.
Weidner, N, "The importance of tumor angiogenesis: the evidence continues to grow", Am J Clin Pathol. Nov. 2004 122(5):696-703.
Yuan, Yading et al., "Correlative feature analysis on FFDM", Medical Physics, vol. 35, No. 12, Nov. 13, 2008, pp. 5492-5494.
Bouget, David, et al., "Vision-based and marker-less surgical tool detection and tracking: a review of the literature", Medical Image Analysis, published Sep. 13, 2016, DOI:https://doi.org/10.1016/j.media.2016.09.003, 29 pages.

* cited by examiner

PERSONALIZED BREAST IMAGING SYSTEM

CROSS-REFERENCE TO RELATED APPLICATIONS

This application is a continuation of U.S. patent application Ser. No. 16/942,268, filed Jul. 29, 2020, now U.S. Pat. No. 11,883,206, which claims priority to U.S. Provisional Patent Application No. 62/879,758, filed Jul. 29, 2019, the entire disclosures of which are incorporated herein by reference in their entireties. To the extent appropriate, a claim of priority is made to each of the above disclosed applications.

BACKGROUND

Modern breast care relies prominently on radiological imaging and the extensive analysis of radiological images. Often, the radiological imaging process poses various challenges. For example, in order to provide high quality images while applying the minimum radiation dose to a patient, sufficient compression needs to be applied to a patient's breast to allow the imaging X-rays to penetrate through all the tissues of the breast. In the ultrasound context, the proper compression enables the ultrasound beam to reach more deep and spreading tissue. However, excessive compression of the breast can cause significant discomfort or pain for the patient.

It is with respect to these and other general considerations that the aspects disclosed herein have been made. Also, although relatively specific problems may be discussed, it should be understood that the examples should not be limited to solving the specific problems identified in the background or elsewhere in this disclosure.

SUMMARY

Examples of the present disclosure describe systems and methods for personalized breast imaging. In aspects, a first set of physical attributes for a patient's breast may be collected. The first set of physical attributes may relate to, or be used to determine, for example, breast size, breast thickness, and/or three-dimensional (3D) breast shape. The first set of physical attributes may be used to customize image acquisition parameters for the patient. A second set of physical attributes for the patient's breast may also be collected. The second set of physical attributes may relate to, or be used to determine, for example, breast elasticity and breast density. The second set of physical attributes may be used to customize breast compression parameters for the patient. The customized image acquisition parameters and breast compression parameters may then be used to perform one or more procedures (e.g., an imaging procedure, a biopsy procedure, etc.) on the patient's breast.

Aspects of the present disclosure provide a system comprising: at least one processor; and memory coupled to the at least one processor, the memory comprising computer executable instructions that, when executed by the at least one processor, performs a method comprising: collecting a first set of attributes for a breast of a patient; customizing image acquisition parameters for the breast of the patient based on the first set of attributes; collecting a second set of attributes for the breast of the patient; customizing compression parameters for the breast of the patient based on the second set of attributes; compressing the breast based on the compression parameters; and imaging the compressed breast using the customized image acquisition parameters for the patient.

Aspects of the present disclosure further provide a method comprising: collecting a first set of data for a breast of a patient; customizing image acquisition parameters for the breast of the patient based on the first set of data; collecting a second set of data for the breast of the patient; customizing compression parameters for the breast of the patient based on the second set of data; compressing the breast based on the compression parameters; and imaging compressed breast using the customized image acquisition parameters for the patient.

Aspects of the present disclosure further provide a method comprising: collecting a first set of data for a patient, wherein the first set of data relates to at least one of: breast size, breast thickness, or breast shape; collecting a second set of physical data for the patient, wherein the second set of data relates to at least one of: breast elasticity or breast density; customizing breast compression parameters for the patient based on the second set of data; compressing a breast of the patient based on the breast compression parameters; customizing image acquisition parameters for the breast based on at least one of the first set of data or the second set of data; and using the customized image acquisition parameters to perform an imaging procedure on the compressed breast.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Additional aspects, features, and/or advantages of examples will be set forth in part in the description which follows and, in part, will be apparent from the description, or may be learned by practice of the disclosure.

BRIEF DESCRIPTION OF THE DRAWINGS

Non-limiting and non-exhaustive examples are described with reference to the following figures.

DETAILED DESCRIPTION

Figure 1:
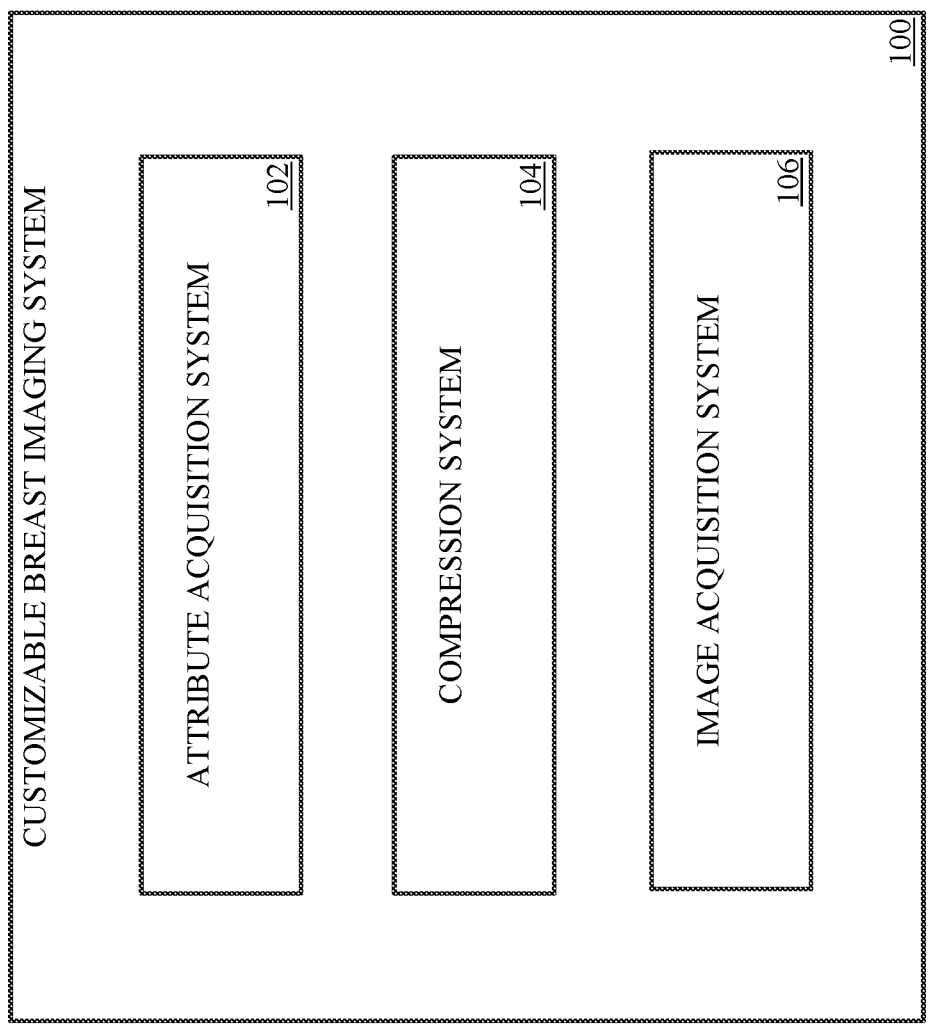
FIG. 1 illustrates an overview of an example system for personalized breast imaging, as described herein.

Medical imaging has become a widely used tool for identifying and diagnosing abnormalities, such as cancers or other conditions, within the human body. Medical imaging processes such as mammography and tomosynthesis are particularly useful tools for imaging breasts to screen for, or diagnose, cancer or other lesions within the breasts. Tomosynthesis systems are mammography systems that allow high resolution breast imaging based on limited angle tomosynthesis. Tomosynthesis, generally, produces a plurality of X-ray images, each of discrete layers or slices of the breast, through the entire thickness thereof. In contrast to conventional two-dimensional (2D) mammography systems, a tomosynthesis system acquires a series of X-ray projection images, each projection image obtained at a different angular displacement as the X-ray source moves along a path, such as a circular arc, over the breast. In contrast to conventional computed tomography (CT), tomosynthesis is typically based on projection images obtained at limited angular displacements of the X-ray source around the breast. Tomosynthesis reduces or eliminates the problems caused by tissue overlap and structure noise present in 2D mammography imaging. Ultrasound imaging is another particularly useful tool for imaging breasts. In contrast to 2D mammography images, breast CT, and breast tomosynthesis, breast ultrasound imaging does not cause a harmful x-ray radiation dose to be delivered to patients. Moreover, ultrasound imaging enables the collection of 2D and 3D images with manual, free-handed, or automatic scans, and produces primary or supplementary breast tissue and lesions information for specific demographic groups or general populations.

Despite the numerous improvements to medical imaging provided by the medical imaging processes described above, various challenges remain. For example, one prominent challenge is balancing the competing factors of minimizing the radiation dose administered to patients while minimizing patient discomfort. On the one hand, to provide high quality medical images while applying the minimum radiation dose to a patient, sufficient compression needs to be applied to a patient's breast to allow the imaging X-rays to penetrate through all the tissues of the breast. In the ultrasound context, sufficient compression needs to be applied to a patient's breast to allow the ultrasound beam to reach more deep and spreading tissue. In the CT context, sufficient compression needs to be applied to a patient's breast to limit or entirely restrict the breast's movement and mobility. On the other hand, excessive compression of the breast can cause significant discomfort or pain for the patient. Although each patient's breast attributes (e.g., size, shape, elasticity, etc.) are different, conventional medical imaging processes and systems are not based on individualized breast attributes. Instead, such processes and systems are based on assumptions of generalized breast attributes, which do not take into account factors such as spatial thickness distributions for the areas of the breast. As a result, such processes and systems implement compression techniques that are uncomfortable or painful to many patients. Moreover, such processes and systems implement imaging processes that may not adequately capture the desired data (e.g., breast tissue amount or section) and/or may provide suboptimal radiation doses to patients.

To address such issues with conventional medical imaging processes and systems, the present disclosure describes systems and methods for personalized breast imaging. In aspects, a first set of physical attributes for a patient's breast may be generated and/or collected using one or more image/depth detection tools. The first set of physical attributes may relate to, or be used to determine, for example, breast size, breast thickness, breast volume, and/or breast shape (e.g., 3D static or dynamic breast shape). Example image/depth detection tools include, but are not limited to, image sensors, depth sensors, tracking sensors, stereo/high-definition (HD) cameras, and infrared cameras. The first set of physical attributes may be used to customize/personalize one or more image acquisition parameters or processes to be used by an imaging system. For example, the first set of physical attributes may be used to optimize an automatic exposure control (AEC) function of a medical radiography device, or to optimize a breast movement/mobility limiting device in breast CT imaging and ultrasound imaging. As another example, the first set of physical attributes may be used to register the breast tissue information of various imaging modality (e.g., 2D/3D ultrasound images, x-ray breast images, etc.) with an image fusion application/service. The registered breast tissue information may be used to construct a fused 3D image of the breast (e.g., 3D depth and shape information).

In aspects, a second set of physical attributes for a patient's breast may also be generated and/or collected using one or more force detection tools. The second set of physical attributes may relate to, or be used to determine, for example, breast elasticity and breast density. Example force detection tools include, but are not limited to, compression sensors, tension sensors, and compression and tensile sensors. The second set of physical attributes may be used to customize/personalize breast compression parameters for the patient. For example, the second set of physical attributes may be used to calculate an optimal (e.g., minimal required) compressive force to be applied by a compression paddle of a medical radiography device during digital breast imaging. In at least one example, the optimal compressive force may be determined/calculated to be no compressive force, or a nominal compressive force. In such an example, a compression paddle may not be used during the image acquisition process.

In aspects, the customized image acquisition parameters and breast compression parameters may be used to perform one or more imaging procedures relating to the patient. As one example, the customized parameters may be provided to a breast imaging system. Based on the received customized parameters, the breast imaging system may perform a breast compression procedure that is personalized for the patient. This personalized breast compression procedure may reduce or eliminate the pain/discomfort typically experienced by the patient during breast imaging. Once the patient's breast has been sufficiently compressed, the breast imaging system may use the customized parameters to generate one or more images of the compressed breast. This customized imaging procedure may provide the best possible image quality at the lowest possible radiation dose. Such a customized imaging procedure may also enable an imaging system to monitor patient motion in real-time. The monitoring of patient motion may enable imaging system operators to quickly determine whether the motion exceeds the clinical allowance for various imaging procedures. When issues are detected with images being generated by the imaging system, imaging system operators may immediately determine whether new images need to be taken while the patient is still on site, thus reducing additional patient visits to the imaging facility.

In some aspects, the customized image acquisition parameters, customized breast compression parameters, and/or one or more breast images may be used to perform one or more medical procedures relating to the patient. As one example, such information may be used to perform a breast biopsy procedure. In such a procedure, the real-time biopsy needle placement may be tracked using various breast images (e.g., 2D, tomosynthesis, and CT images) to enable accurate tissue extraction. Alternately, one or more ultrasound images may be used during such procedures. For instance, the 3D breast shape and volume data may be used with a hand-held ultrasound probe or combined with volumetric ultrasound scanning in supine or prone breast position.

Accordingly, the present disclosure provides a plurality of technical benefits including, but not limited to: identifying personalized physical breast attributes, using personalized physical breast attributes to customize imaging acquisition parameters, using personalized physical breast attributes to customize breast compression parameters, optimizing the required radiation dose delivered to patients during medical imaging procedures, minimizing the discomfort/pain experienced by patients during medical imaging procedures, real-time monitoring of patient motion during medical imaging procedures, reducing patient call-backs and visits, implementing comprehensive, multimodal breast care assessment.

FIG. 1 illustrates an overview of an example system for personalized breast imaging as described herein. Example system 100 as presented is a combination of interdependent components that interact to form an integrated system for performing personalized breast imaging and related procedures. Components of the system may be hardware components (e.g., used to execute/run operating system (OS)) or software components (e.g., applications, application programming interfaces (APIs), modules, virtual machines, runtime libraries, etc.) implemented on, and/or executed by, hardware components of the system. In one example, example system 100 may provide an environment for software components to run, obey constraints set for operating, and utilize resources or facilities of the system 100. For instance, software may be run on a processing device such as a personal computer (PC), mobile device (e.g., smart device, mobile phone, tablet, laptop, personal digital assistant (PDA), etc.), and/or any other electronic devices. As an example of a processing device operating environment, refer to the example operating environments depicted in FIG. 4. In other examples, the components of systems disclosed herein may be distributed across multiple devices. For instance, input may be entered on a client device, data may be collected using one or more medical devices, and information may be processed or accessed using other computing devices.

As one example, system 100 may comprise attribute acquisition system 102, compression system 104, and image acquisition system 106. One of skill in the art will appreciate that the scale of systems such as system 100 may vary and may include more or fewer components than those described in FIG. 1. For instance, in some examples, the functionality and/or components of attribute acquisition system 102 may be distributed across multiple systems and devices.

Attribute acquisition system 102 may be configured to identify and/or collect data relating to one or more physical attributes of a patient's breast. In aspects, attribute acquisition system 102 may comprise one or more sensor components, such as image sensors, depth sensors, tracking sensors, proximity sensors, stereo/HD cameras, and infrared cameras. The sensor components may be used to collect a first set of data and/or images relating to physical attributes of the patient's breast, such as breast size, breast thickness, breast volume, and/or breast shape. The first set of data may be used to reconstruct or estimate the 3D shape of the breast in static and/or dynamic states. Reconstructing/estimating the 3D shape of the breast may comprise applying one or more 3D models or algorithms to the first set of data. For example, a 3D model implementing a stereo depth algorithm may use various 3D coordinates of breast surface points to estimate the 3D breast shape. A model, as used herein, may refer to a predictive or statistical utility or program that may be used to determine a probability distribution over one or more character sequences, classes, objects, result sets or events, and/or to predict a response value from one or more predictors. A model may be based on, or incorporate, one or more rule sets, machine learning, a neural network, reinforcement learning, or the like. As another example, a computer vison or neural network-based algorithm may be used to calculate the 3D depth and shape information for a breast based on the acquired breast image data. In some examples, the 3D modelling techniques or algorithms may be implemented by attribute acquisition system 102. In other examples, attribute acquisition system 102 may access and/or or execute the 3D modelling techniques or algorithms on remote devices or using an accessible service.

Compression system 104 may be configured to identify and/or collect data relating to one or more physical attributes of a patient's breast. In aspects, compression system 104 may comprise one or more sensor components, such as compression sensors, tension sensors, and compression and tensile sensors. The sensor components may be used to collect a second set of data relating to physical attributes of the patient's breast, such as breast elasticity and breast density. For example, a compression paddle of a medical radiography device may comprise one or more force sensors. The compression paddle may apply at least a partial compression to a patient's breast. Based on the compression measurements acquired during this partial compression, the elasticity and density of the breast may be computed. Computing the elasticity and/or density may comprise applying one or more compression models or algorithms to the second set of data. As one example, a compression algorithm may use the pressure applied over an estimated contact area of the breast and other breast attribute data (e.g., the volume of fibroglandular tissue, total breast tissue volume, etc.) to determine volumetric breast density. In examples, the compression models or algorithms may be implemented locally by attribute acquisition system 102 or accessed remotely over a distributed network. Based on the computing breast elasticity and/or density, compression system 104 may apply an optimal compression force to the patient's breast. The optimal compression force may represent the minimum compression force required to stabilize the patient's breast and acquire the desired image quality.

Image acquisition system 106 may be configured to generate one or more breast images. In aspects, image acquisition system 106 may implement functionality to execute one or more imaging modalities, such as 2D imaging (such as mammography), tomosynthesis, CT imaging, and ultrasound imaging. The functionality may be implemented by an imaging device, such as a digital mammography unit. In examples, such an imaging device may comprise a gantry assembly. The gantry assembly may be configured as a circular, rotating frame comprising an X-ray tube mounted on one side of the frame and an X-ray detector located on the opposite side of the frame. Alternately, the gantry assembly may be configured as a substantially straight segment upon which a medical imaging device, such as a C-arm, is attached. In aspects, image acquisition system 106 may receive, or otherwise have access to, data collected by attribute acquisition system 102 and/or compression system 104. Based on at least a portion of the collected data, image acquisition system 106 may set one or more customized imaging parameters for the patient, such as a scanning angle range or techniques, an X-ray dose, or scan areas or volumes. Using the customized imaging parameters, image acquisition system 106 may generate and/or present one or more breast images for the patient.

In some aspects, image acquisition system 106 may be further configured to evaluate the generated images and/or events during the image acquisition process. As one example, image acquisition system 106 may monitor patient motion and breast dynamic shape changes during the image acquisition process. Image acquisition system 106 may evaluate the patient motion using an algorithm based on images and image sequence analysis or a motion capture component (not pictured) to determine whether the extent of the motion exceeds the clinical allowance for the particular procedure being performed. As another example, image acquisition system 106 may compare the generated images to the image data collected/generated by image acquisition system 106 to verify the clarity/quality of the generated images. In such an example, if image acquisition system 106 indicates that the generated images are deficient or substandard, an indication may be provided to the imaging device operator in real-time; thus, enabling the operator to re-perform at least a portion of the image acquisition process.

In some aspects, image acquisition system 106 may be further configured to facilitate the performance of one or more medical procedures relating to the patient. As one example, image acquisition system 106 may be used during a breast biopsy procedure to track real-time needle placement. Such tracking may enable physicians to accurately perform manual or automated tissue extraction. As another example, during a medical procedure, the rigid pose of a hand-held ultrasound probe and/or interventional instruments may be accurately tracked in real-time. The images representing the tracked probe may be fused with, for example, 2D mammography and tomosynthesis X-ray images using geometric image registration. The fused images may provide real-time visual information for automatic mechanical scans and/or free-styled manual scans.

Figure 2:
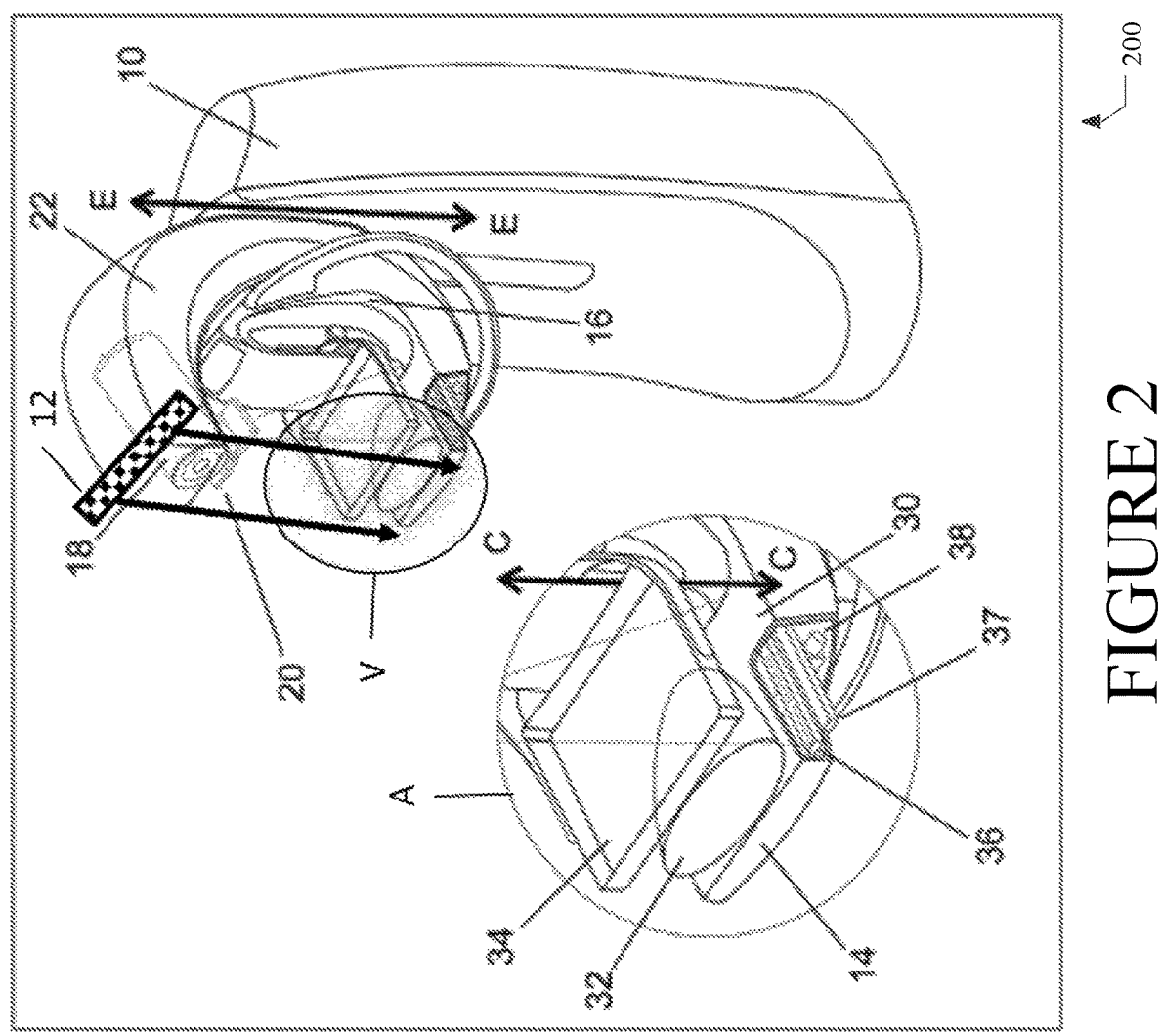
FIG. 2 illustrates an overview of an example imaging system for personalized breast imaging, as described herein.

FIG. 2 illustrates an overview of an example imaging system 200 for personalized breast imaging, as described herein. The data collection and imaging techniques implemented by input processing system 200 may comprise the data collection and imaging techniques and data described in the system of FIG. 1. In some examples, one or more components of imaging system 200 (or the functionality thereof) may be distributed across multiple devices and/or systems. In other examples, a single device having an alternate physical configuration may comprise the components of imaging system 200.

With respect to FIG. 2, imaging system 200 may comprise system gantry 10, imaging sensor 12, X-ray detector assembly 14, compression paddle driver 16, X-ray tube 18, X-ray collimator 20, C-arm 22, breast platform 30, breast compression/stabilization paddle 34, X-ray anti-scatter grid 36, X-ray thin film transistor (TFT) detector 37, and detector driver 38. System gantry 10 may be a structure configured to physically support one or more imaging devices, such as C-arm 22. In alternate configuration, system gantry 10 may be configured as a circular, rotating frame comprising the one or more imaging devices. C-arm 22 may be configured to affix to system gantry 10 such that C-arm 22 may be manipulated about a vertical plane (plane E) of system gantry 10.

Imaging sensor 12 may be configured to dynamically capture images and/or physical attribute data of a patient breast 32. For example, imaging sensor 12 may use stereo depth sensors to capture data relating to dynamic 3D shape measurements and optical HD images of patient breast 32. In aspects, imaging sensor 12 may be positioned such that image data may be captured for objects placed on or near breast platform 30. As one example, imaging sensor 12 may be positioned such that a top-down view of a patient's breast is observable. For instance, in FIG. 2, the volume of space for which 3D object surface points may be accurately determined by imaging sensor 12 is represented by volume V (view A presents a more detailed view of volume V). The data captured by imaging sensor 12 may be stored in a data store located on, or accessible to, one or more components of system gantry 10. In some examples, at least a portion of the data captured by imaging sensor 12 may be provided to a 3D modeling algorithm or service. The 3D modeling algorithm or service may use the data to construct a 3D representation of patient breast 32.

Compression paddle driver 16 may be configured to manipulate, or facilitate manipulation of, the motion of breast compression/stabilization paddle 34. In aspects, compression paddle driver 16 may comprise, or have access to, settings or instructions for causing breast compression/stabilization paddle 34 to apply an amount of compressive force to patient breast 32. The settings or instructions may be specific to each patient or generically applied to all patients. For example, settings comprising a generic set of compression parameters may be applied to all patients during an initial breast elasticity analysis. Based on the results of the breast elasticity analysis, a personalized set of compression parameters may be applied to each patient.

Breast compression/stabilization paddle 34 may be configured to apply compressive force to a patient breast positioned on breast platform 30. The compressive force may be used to stabilize the patient breast and/or to at least partially compress the patient breast. In examples, compression/stabilization paddle 34 may comprise a rigid compression surface, such as hard polycarbonate material. Alternately or additionally, breast compression/stabilization paddle 34 may comprise a semi-rigid or pliable compressive element, such as foam. Stabilizing paddles utilizing foam compressive elements are described in, for example, WO 2019/227042 A1, the disclosure of which is hereby incorporated by reference herein in its entirety. As one specific example, foam may be secured to a hard plastic compression paddle substrate with a radiotranslucent adhesive, or may be mechanically secured thereto, for example, with hooks, straps, or other securement structures. In other examples, foam may also be placed underneath the breast (e.g., secured to breast platform 30). The foam may at least partially conform in shape to the patient breast as the paddle is lowered and the foam compresses. The conformity of the foam to the patient breast may enable stabilization of the patient breast for imaging, without requiring the compression pressure typical in breast imaging systems. Accordingly, the foam may be utilized to stabilize and/or compress the patient breast to an imaging condition, instead of necessarily effectuating full compression of the patient breast. That is, the imaging condition need only be consistent with a thickness where the resultant tomosynthesis images are a manageable number. Such a manageable number may be a diagnostically significant number, such that the resulting breast image slices may provide sufficient distinction between slices, but without having such a large number of images, which would necessitate significantly more review time by a clinician.

Breast compression/stabilization paddle 34 may further comprise one or more force-based sensors for detecting the compressive force being applied by breast compression/stabilization paddle 34. As breast compression/stabilization paddle 34 is manipulated about a vertical plane (plane C) of gantry system 10, the force-based sensors may collect compressive force measurements for patient breast 32. In some examples, at least a portion of the compressive force measurements may be provided to a density analysis algorithm or service. The density analysis algorithm or service may use the data to determine the breast density and/or elasticity of the compressed breast. The compressive force measurements and/or the determined breast density/elasticity may be stored in a data store, such as the data store described above.

X-ray tube 18 and X-ray collimator 20 may be configured to deliver a radiation dose to patient breast 32. In aspects, gantry system 10 may have access to a set of personalized imaging parameters. The personalized imaging parameters may be optimized for patient breast 32. For example, the personalized imaging parameters may ensure that a sufficient amount of breast tissue is imaged, and a minimum radiation dose is applied to patient breast 32. The personalized imaging parameters may be used to cause X-ray tube 18 to generate a particular radiation dose. X-ray detector assembly 14 may be configured to detect and/or record the radiation dose delivered to patient breast 32 and/or a corresponding radiograph. X-ray detector assembly 14 may comprise X-ray TFT detector 37 and X-ray anti-scatter grid 36. X-ray TFT detector 37 may be configured to detect and/or record a radiograph corresponding to a delivered radiation dose. X-ray anti-scatter grid 36 may be configured to limit the amount of radiation scatter received by X-ray detector assembly 14.

Having described various systems that may be employed by the aspects disclosed herein, this disclosure will now describe one or more methods that may be performed by various aspects of the disclosure. In aspects, method 300 may be executed by an example system, such as system 100 of FIG. 1 or input processing system 200 of FIG. 2. In examples, method 300 may be executed on a device comprising at least one processor configured to store and execute operations, programs, or instructions. However, method 300 is not limited to such examples. In other examples, method 300 may be performed on an application or service for personalized breast imaging. In at least one example, method 300 may be executed (e.g., computer-implemented operations) by one or more components of a distributed network, such as a web service/distributed network service (e.g., cloud service).

Figure 3:
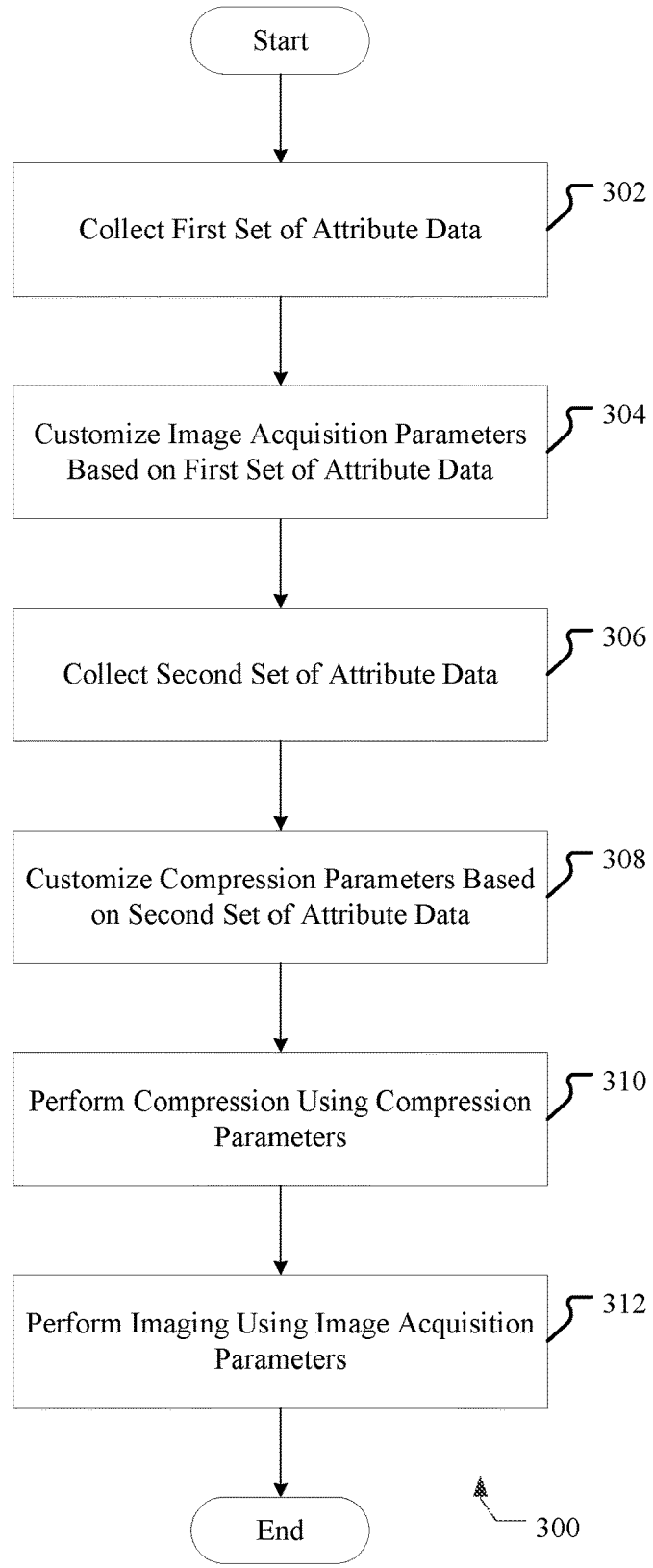
FIG. 3 illustrates an example method for personalized breast imaging, as described herein.

FIG. 3 illustrates an example method 300 for personalized breast imaging, as described herein. Example method 300 begins at operation 302, where a first set of patient attribute data may be collected. In aspects, a breast imaging system may implement an attribute collection device or system, such as attribute acquisition system 102. The attribute collection device or system may be used to generate and/or collect a first set of physical attribute data relating to a patient's breast. The first set of physical attributes may relate to the size, thickness, volume, and/or shape of the breast. As a specific example, the attribute collection device/system may be a stereo vision camera comprising one or more depth sensors. The stereo vision camera may be affixed to (or otherwise integrated into) a breast imaging unit. The stereo vision camera may be used to capture dynamic HD image data and depth data for a patient's breast. As another example, the attribute collection device/system may a single camera, such as a smart phone camera, a digital camera, an infrared camera, or the like. The single camera may be used to capture multiple 2D images. The 2D images may be used to train a machine learning algorithm to estimate the 3D breast size and shape.

At operation 304, image acquisition parameters for the patient may be customized. In aspects, based on the first set of physical attribute data, one or more attributes of the patient's breast may be determined. The determined attributes may be used to personalize one or more image acquisition parameters used by the breast imaging system. For example, the first set of physical attribute data may be used to determine the thickness and the 3D shape of the breast. The determined breast thickness may be used to optimize a current AEC function of the breast imaging system. The optimization of the current AEC function, which depends on the selected X-ray techniques (e.g., kVp/Filter/mAs), may enable the patient dose to be estimated more accurately for each patient. In at least one example, for tomosynthesis imaging, the determined breast thickness may be used to identify the optimal number range of X-ray image slices used for breast volume reconstruction. The identified number range may ensure that the entire breast volume is reconstructed while reducing the amount unnecessary X-ray image slices depicting regions outside of the breast; thereby, improving clinical throughput. The 3D shape of the breast may be used to, for example, estimate breast volume and breast tissue coverage to determine the amount (or section) of breast tissue to be imaged. Additionally, the 3D shape of the breast may be used to determine the spatial thickness distribution of the dose. Such information may be used to customize breast imaging parameters, such as scanning angle range and X-ray dose in tomosynthesis and CT scans.

At operation 306, a second set of patient attribute data may be collected. In aspects, the breast imaging system may further implement a breast compression device or system, such as compression system 104. The compression device or system may be used to generate and/or collect a second set of physical attribute data relating to a patient's breast. The second set of physical attributes may relate to the density and elasticity of the breast. As a specific example, the compression device/system may be a compression/stabilization paddle of the breast imaging system. The compression/stabilization paddle may comprise a set of force sensors used to capture force measurements during stabilization and/or a compression of the patient's breast. In aspects, the compression device or system may be configured to operate in a breast assessment mode, during which a partial compression of the breast is performed. The force measurements acquired during the partial compression may be used to compute the breast elasticity and/or density in real-time (or in near real-time).

At operation 308, compression parameters for the patient may be customized. In aspects, based on the second set of physical attribute data, one or more attributes of the patient's breast may be determined. The determined attributes may be used to personalize one or more compression parameters used by the breast imaging system. For example, the second set of physical attribute data may be used to determine the optimal compression force to apply to the patient's breast during an imaging procedure. The optimal compression force may represent the minimal compression force required to stabilize the breast during the imaging procedure, while allowing the desired image quality to be achieved. At operation 310, the patient's breast may be compressed based on the customized compression parameters for the patient. In aspects, the compression device or system may use the customized compression parameters to perform a compression of the patient's breast.

At operation 312, a breast imaging procedure may be performed on the compressed, breast. In aspects, the breast imaging system may further implement an image acquisition device or system, such as image acquisition system 106. The image acquisition device or system may be used to produce one or more images of the patient's compressed or movement-limited/locked breast based on the image acquisition parameters determined at operation 304 and/or the compression parameters determined at operation 308. As a specific example, a digital mammography device may use a set of personalized image acquisition parameters to generate one or more tomosynthesis or CT images of a patient's compressed breast. In some aspects, the breast imaging system may monitor the patient's motion during the imaging procedure. If the patient's motion exceeds a clinical allowance for the selected imaging procedure, the operator of the breast imaging system may be notified using, for example, an audio, a visual, or a tactile indication (e.g., an audible tone, a blinking light or message notification, a vibration, etc.). Such a notification may enable the operator to re-perform the imaging procedure while the patient is still on site; thereby, reducing patient callbacks and visits.

In at least one aspect, at least a portion of the first set of patient attribute data, the second set of patient attribute data, and/or the images produced at operation 312 may additionally be used in one or more alternate procedures. As on example, a set of X-ray images, ultrasound images, and/or optical stereo/HD images may be combined using an image fusion algorithm. The fusion process may be performed by the breast imaging system or by a system accessible to the breast imaging system. The fused images may be used during a breast biopsy to track biopsy needle placement in real-time; thereby, enabling a physician to accurately perform manual or automated tissue extraction.

Figure 4:
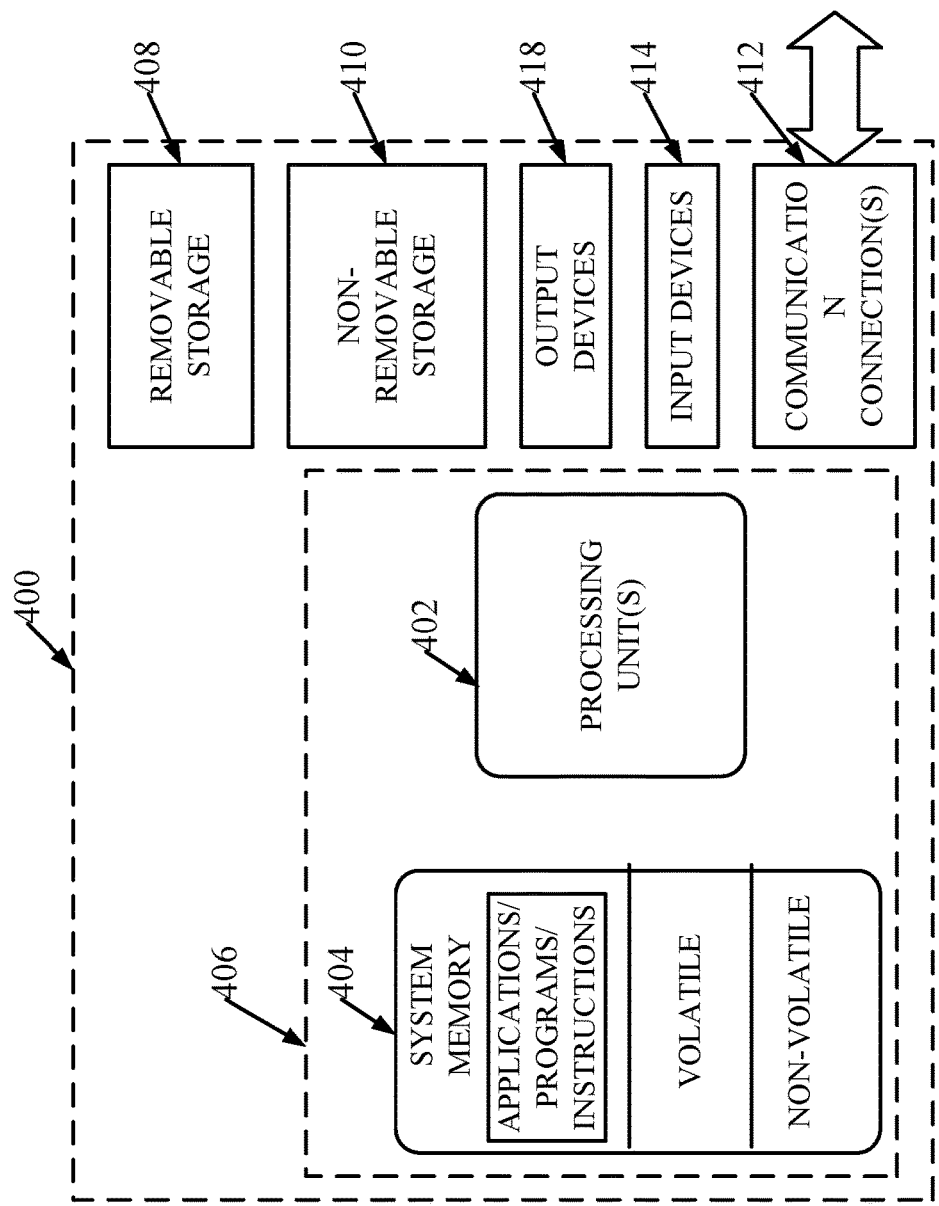
FIG. 4 illustrates one example of a suitable operating environment in which one or more of the present embodiments may be implemented.

FIG. 4 illustrates an exemplary suitable operating environment for detecting X-ray tube output roll off described in FIG. 1. In its most basic configuration, operating environment 400 typically includes at least one processing unit 402 and memory 404. Depending on the exact configuration and type of computing device, memory 404 (storing, instructions to perform the X-ray tube roll off detection techniques disclosed herein) may be volatile (such as RAM), non-volatile (such as ROM, flash memory, etc.), or some combination of the two. This most basic configuration is illustrated in FIG. 4 by dashed line 406. Further, environment 400 may also include storage devices (removable, 408, and/or non-removable, 410) including, but not limited to, magnetic or optical disks or tape. Similarly, environment 400 may also have input device(s) 414 such as keyboard, mouse, pen, voice input, etc. and/or output device(s) 416 such as a display, speakers, printer, etc. Also included in the environment may be one or more communication connections 412, such as LAN, WAN, point to point, etc. In embodiments, the connections may be operable to facility point-to-point communications, connection-oriented communications, connectionless communications, etc.

Operating environment 400 typically includes at least some form of computer readable media. Computer readable media can be any available media that can be accessed by processing unit 402 or other devices comprising the operating environment. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other non-transitory medium which can be used to store the desired information. Computer storage media does not include communication media.

Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared, microwave, and other wireless media. Combinations of the any of the above should also be included within the scope of computer readable media.

The operating environment 400 may be a single computer operating in a networked environment using logical connections to one or more remote computers. The remote computer may be a personal computer, a server, a router, a network PC, a peer device or other common network node, cloud server, data center, and typically includes many or all of the elements described above as well as others not so mentioned. The logical connections may include any method supported by available communications media. Such networking environments are commonplace in offices, enterprise-wide computer networks, intranets and the Internet.

The embodiments described herein may be employed using software, hardware, or a combination of software and hardware to implement and perform the systems and methods disclosed herein. Although specific devices have been recited throughout the disclosure as performing specific functions, one of skill in the art will appreciate that these devices are provided for illustrative purposes, and other devices may be employed to perform the functionality disclosed herein without departing from the scope of the disclosure.

This disclosure describes some embodiments of the present technology with reference to the accompanying drawings, in which only some of the possible embodiments were shown. Other aspects may, however, be embodied in many different forms and should not be construed as limited to the embodiments set forth herein. Rather, these embodiments were provided so that this disclosure was thorough and complete and fully conveyed the scope of the possible embodiments to those skilled in the art.

Although specific embodiments are described herein, the scope of the technology is not limited to those specific embodiments. One skilled in the art will recognize other embodiments or improvements that are within the scope and spirit of the present technology. Therefore, the specific structure, acts, or media are disclosed only as illustrative embodiments. The scope of the technology is defined by the following claims and any equivalents therein.

What is claimed is:

1. An imaging system for imaging a breast of a patient, the imaging system comprising:
    an x-ray imaging device including an x-ray tube and an x-ray detector;
    a breast compression device including a paddle and a platform;
    at least one processor; and
    memory coupled to the at least one processor, the memory comprising computer executable instructions that, when executed by the at least one processor, performs a set of operations comprising:
        receiving a first set of physical attributes for the breast of the patient, wherein the first set of physical attributes are specific to the patient and comprise at least one of breast size, breast thickness, breast shape, breast volume data, and breast surface points;
        customizing image acquisition parameters for the x-ray imaging device specific for the breast of the patient based on the first set of physical attributes, wherein the image acquisition parameters include automatic exposure control function, a spatial thickness distribution of tissue, and a desired number range of image slices used for breast volume reconstruction, the number of slices being based on breast thickness;

receiving a second set of physical attributes for the breast of the patient, wherein the second set of physical attributes comprise at least one of breast elasticity, breast composition distributions, and breast density; and customizing compression parameters for the breast compression device specific for the breast of the patient based on at least one of the first set of physical attributes and the second set of physical attributes;

wherein the breast compression device is configured to compress the breast of the patient based on the customized compression parameters for the breast of the patient and the x-ray imaging device is configured to image the breast of the patient based on the customized image acquisition parameters for the breast of the patient, and wherein the memory is configured to store the first set of physical attributes for the breast of the patient, the customized image acquisition parameters for the breast of the patient, the second set of physical attributes for the breast of the patient, and the customized compression parameters for the breast of the patient.

2. The imaging system of claim 1, wherein the customized compression parameters for the breast compression device are only based on the second set of physical attributes.

3. The imaging system of claim 1, wherein the first set of physical attributes include breast size.

4. The imaging system of claim 3, wherein the set of operations further includes collecting one or more images for determination of breast size.

5. The imaging system of claim 4, further comprising at least one imaging device used to collect the one or more images.

6. The imaging system of claim 1, wherein the set of operations further includes collecting one or more images for generating at least some of the first set of physical attributes.

7. The imaging system of claim 6, further comprising a stereo depth sensor, an HD camera, a tracking sensor, a computer vision algorithm, or a machine learning algorithm used to collect the one or more images.

8. The imaging system of claim 1, wherein the set of operations further includes:
applying, to the at least one of the first set of physical attributes and the second set of physical attributes for the breast of the patient, a compression algorithm for determining breast compression force; and
receiving, as output from the compression algorithm, an optimal compression force for the breast of the patient.

9. The imaging system of claim 8, wherein the optimal compression force for the breast of the patient represents a minimum compression force required to stabilize the breast of the patient and acquire a desired image quality.

10. The imaging system of claim 1, wherein the set of operations further includes:
imaging the breast of the patient using the customized image acquisition parameters; and
receiving as output from the imaging, one or more breast images.

11. The imaging system of claim 1, a wherein the paddle has one or more compression force sensors.

12. A method for imaging a breast of a patient, the method comprising:
receiving a first set of physical attributes for the breast of the patient at an imaging system, wherein the first set of physical attributes are specific to the patient and comprise at least one of breast size, breast thickness, breast shape, breast volume data, and breast surface points;

customizing image acquisition parameters for an x-ray imaging device of the imaging system specific for the breast of the patient based on the first set of physical attributes, wherein the image acquisition parameters include automatic exposure control function, a spatial thickness distribution of tissue, and a desired number range of image slices used for breast volume reconstruction, the number of slices being based on breast thickness;

receiving a second set of physical attributes for the breast of the patient at the imaging system, wherein the second set of physical attributes comprise at least one of breast elasticity, breast composition distributions, and breast density;

customizing compression parameters for a breast compression device of the imaging device specific for the breast of the patient based on at least one of the first set of physical attributes and the second set of physical attributes;

compressing the breast of the patient at the breast compression device based on the customized compression parameters for the breast of the patient;

imaging the breast of the patient via the x-ray imaging device based on the customized image acquisition parameters for the breast of the patient; and storing the first set of physical attributes for the breast of the patient, the customized image acquisition parameters for the breast of the patient, the second set of physical attributes for the breast of the patient, and the customized compression parameters for the breast of the patient.

13. The method of claim 12, wherein the customized compression parameters for the breast compression device are only based on the second set of physical attributes.

14. The method of claim 12, wherein the first set of physical attributes include breast size.

15. The method of claim 14, further comprising collecting one or more images for determination of breast size.

16. The method of claim 12, further comprising collecting one or more images for generating at least some of the first set of physical attributes.

17. The method of claim 12, further comprising:
applying, to the at least one of the first set of physical attributes and the second set of physical attributes for the breast of the patient, a compression algorithm for determining breast compression force; and
receiving, as output from the compression algorithm, an optimal compression force for the breast of the patient.

18. The method of claim 17, wherein the optimal compression force for the breast of the patient represents a minimum compression force required to stabilize the breast of the patient and acquire a desired image quality.

19. The method of claim 12, further comprising
generating, during the imaging of the compressed breast, one or more breast images;
registering breast tissue identified in the one or more breast images; and fusing the registered breast tissue to create one or more fused breast images.

20. The method of claim 12, further comprising monitoring patient movement in real-time.

* * * * *